United States Patent
Schneidersmann et al.

(10) Patent No.: US 6,503,904 B2
(45) Date of Patent: Jan. 7, 2003

(54) PESTICIDAL COMPOSITION FOR SEED TREATMENT

(75) Inventors: Ferdinand Martin Schneidersmann, Calgary (CA); Marian Ladislav Stypa, Cambridge (CA)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/094,840

(22) Filed: Mar. 8, 2002

(65) Prior Publication Data

US 2002/0137759 A1 Sep. 26, 2002

Related U.S. Application Data

(63) Continuation of application No. 09/441,691, filed on Nov. 16, 1999, now abandoned.
(60) Provisional application No. 60/172,242, filed on Nov. 16, 1998.

(51) Int. Cl.[7] .................. A01N 43/40; A01N 43/64; A01N 43/36; A01N 32/12; A61K 31/535
(52) U.S. Cl. .............. 514/229.2; 514/341; 514/357; 514/383; 514/422; 514/538
(58) Field of Search ............... 514/229.2, 422, 514/538, 383, 357, 341

(56) References Cited

U.S. PATENT DOCUMENTS

| 4,151,299 A | 4/1979 | Hubele ............... 424/309 |
|---|---|---|
| 4,705,800 A | 11/1987 | Nyfeler et al. ........... 514/422 |
| 4,849,432 A | 7/1989 | Shiokawa et al. .......... 514/341 |
| 5,266,585 A | 11/1993 | Hubele ................. 514/383 |
| 5,843,982 A | 12/1998 | Leadbitter ............. 514/422 |
| 5,852,012 A | 12/1998 | Maienfisch et al. ...... 514/229.2 |
| 6,114,362 A | 9/2000 | Dutzmann et al. ......... 514/341 |

FOREIGN PATENT DOCUMENTS

| EP | 235725 | 9/1987 |
|---|---|---|
| EP | 376279 | 7/1990 |
| EP | 580553 | 1/1994 |
| WO | WO 97/22254 | 6/1997 |

OTHER PUBLICATIONS

The Pesticide Manual, 10th Edition, The British Crop Protection Council, London, pp. 328–330 (1994).

The Pesticide Manual, 11th Edition, The British Crop Protection Council, London, pp. 545–547, 566–568, 706–708, 792–794, 794–795 and 880–881 (1997).

*Primary Examiner*—Allen J. Robinson
(74) *Attorney, Agent, or Firm*—William A. Teoli, Jr.; Rose M. Allen

(57) ABSTRACT

The present invention provides an at least quaternary composition for controlling insects or representatives of the order Acarina and microorganisms, which composition comprises: (A) an insecticidally effective amount of at least one neonicotinoid or phenylpyrazole insecticide, and (B) a fungicidally effective amount of at least three fungicides including: (B1) at least one phenylainde (acylalanine type), (B2) at least one phenylpyrrole and (B3) at least one triazole.

10 Claims, No Drawings

PESTICIDAL COMPOSITION FOR SEED TREATMENT

This application is a continuation of Ser. No. 09/441,691, filed Nov. 16, 1999, now abandoned, which claims benefit of Ser. No. 60/172,242, filed Nov. 16, 1998, now bandoned.

FIELD OF THE INVENTION

The present invention relates to an at least quaternary pesticidal composition that is suitable for controlling insects and/or representatives of the order Acarina and microorganisms, especially phytopathogenic fungi, comprising (a) at least one insecticide and (b) at least three fungicides. The pesticidal composition is particularly suitable for the protection of plant propagation materials.

BACKGROUND OF THE INVENTION

Certain mixtures of active ingredients for controlling pests are described in the literature. The biological properties of those known mixtures are not entirely satisfactory in the area of pest control, toxicity, pest resistance and loading rates. The protection of plant propagation materials (seed treatments) with pesticides are target applications which partially address the need for a reduction of environmental and worker exposure and pest resistance buildup when used alone or in conjunction with foliar or furrow pesticide applications. However, there is also a need to make available other mixtures which reduce the need for older acutely toxic insecticides and to reduce loading rates. Among the older insecticides, the following may be mentioned: tefluthrin, terbufos, cypermethrin, thiodicarb, lindane, furathiocarb, acephate, butocarboxim, carbofuran, NTN, endosulfan, diethion, aldoxycarb, methiocarb, oftanol, (isofenphos), chlorpyrifos, bendiocarb, benfuracarb, oxamyl, parathion, capfos, dimethoate, fonofos, chlorfenvinphos, cartap, fenthion, fenitrothion, HCH, deltamethrin, malathion, disulfoton. Accordingly, there is a need to provide pesticide compositions and methods for the protection of plant propagation materials, especially those compositions having improved biological properties, for example synergistic pesticidal properties, especially for controlling insects and representatives of the order Acarina and microorganisms. That problem is solved according to the invention by the provision of the present at least quaternary pesticidal composition.

SUMMARY OF THE INVENTION

The present invention provides an at least quaternary composition for controlling insects or representatives of the order Acarina and microorganisms, which composition comprises: (A) at least one insecticidally or acaricidally active compound, and (B) at least three fungicidally active compounds.

More specifically, the present invention provides an at least quaternary composition for controlling insects or representatives of the order Acarina and microorganisms, especially phytopathogenic fungi, that is particularly suitable for the protection of plant propagation materials such as crop seeds; including oil seeds (especially canola (rape) seed). The at least quaternary pesticidal composition of the present invention comprises: (A) an insecticidally effective amount of at least one neonicotinoid or phenylpyrazole insecticide, and (B) a fungicidally effective amount of at least three fungicides including: (B1) at least one phenylamide (acylalanine type), (B2) at least one phenylpyrrole and (B3) at least one triazole.

The invention also relates to a process for protecting the plant propagation materials and the plants resulting therefrom against insects and fungal diseases using a pesticidal composition according to the invention. It also relates to the said plant propagation materials coated with the said pesticidal composition.

The present invention makes it possible to dress or treat seeds and other plant propagation materials with lower amounts of older acutely toxic biocides than is known from the prior art and, in most cases, replaces such older acutely toxic biocides; the invention therefore represents a material enrichment of the art.

DESCRIPTION OF SPECIFIC EMBODIMENTS

Insecticide Component (A)

Preferred are at least quaternary pesticidal compositions comprising as insecticidally active ingredient (A):

at least one neonicotinoid compound of formula (I)

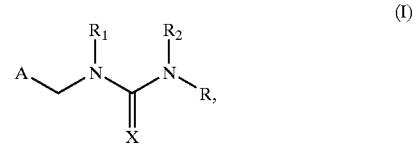

wherein
A is 2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyl-tetrahydrofuran-3-yl or 2-chlorothiazol-5-yl group,
R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl;
$R_1$ and $R_2$ are independently of each other $C_1$–$C_4$-alkyl, $C_1$–$C_4$-alkenyl, $C_1$–$C_4$-alkinyl, —C(=O)—$CH_3$ or benzyl; or together form a group —$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$— or —$CH_2$—N($CH_3$)—$CH_2$—; and X is N—$NO_2$ or N—CN or CH—$NO_2$; , or, where appropriate, a tautomer thereof, in each case from or in salt form; or at least one phenylpyrazole compound of formula (II)

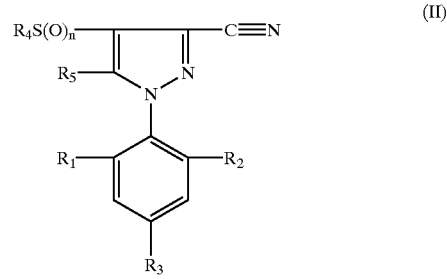

wherein
$R_1$ and $R_2$ may represent a hydrogen or halogen atom (at least one of them is preferably other than hydrogen),
$R_3$ may represent a halogen atom or a haloalkyl or haloalkoxy or $SF_5$ group, in the 4 position on the phenyl ring,
$R_4$ may represent an alkyl or haloalkyl group, $R_5$ may represent an amino group which may be mono- or di- substituted by an alkyl or haloalkyl radical, acyl, alkoxycarbonyl, and n is 0, 1 or 2; in free from or in salt form.

The compounds (I) may be in the form of tautomers. Accordingly, hereinbefore and hereinafter, where appropriate the compound compounds (I) are to be understood to include corresponding tautomers, even if the latter are not specifically mentioned in each case.

The compounds (I) to (II) are capable of forming acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, $C_1$–$C_4$alkanecarboxylic acids, for example acetic acid, saturated or unsaturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halo-substituted, $C_1$–$C_4$alkane- or aryl-sulfonic acids, for example methane- or p-toluene-sulfonic acid. Furthermore, compounds of formula (I) or (II) having at least one acidic group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono-, di- or tri-hydroxy-lower alkylamine, for example mono-, di- or tri-ethanolamine. In addition, corresponding internal salts may also be formed. Preference is given within the scope of the invention to agrochemically advantageous salts. In view of the close relationship between the compounds of formula (I) and (II) in free form and in the form of their salts, any reference hereinbefore or hereinafter to the free compounds of formula (I) and (II) or to their respective salts is to be understood as including also the corresponding salts or the free compounds of formula (I) and (II), where appropriate and expedient. The same applies in the case of tautomers of compounds of formula (I) and (II) and the salts thereof. The free form is generally preferred in each case.

Preferred compounds of the formula (I) are those wherein

A is a pyrid-3-yl, 2-chloropyrid-5-yl, 2-chloro-1-oxido-5-pyridinio or 2-chlorothiazol-5-yl group; particularly a 2-chloropyrid-5-yl group or preferably a 2-chlorothiazol-5-yl group;

wherein R is $C_1$–$C_6$alkyl, phenyl-$C_1$–$C_4$alkyl, $C_3$–$C_4$alkenyl or $C_3$–$C_4$alkynyl; more especially $C_1$–$C_4$alkyl, preferably methyl;

$R_1$ and $R_2$ are independently of each other $C_1$–$C_4$-alkyl or benzyl, or together a group —CH$_2$—CH$_2$—, —CH$_2$—CH$_2$—CH$_2$—, —CH$_2$—O—CH$_2$—, —CH$_2$—S—CH$_2$—, —CH$_2$—NH—CH$_2$—, —CH$_2$—N(CH$_3$) group —CH$_2$—CH$_2$— or —CH$_2$—O—CH$_2$—, particularly —CH$_2$—O—CH$_2$—; and X is N—NO$_2$ or N—CN, more especially N—NO$_2$.

Especially preferred is an at least quaternary pesticidal composition comprising an insecticidally effective amount of a compound selected from the group consisting of: a compound of the formula

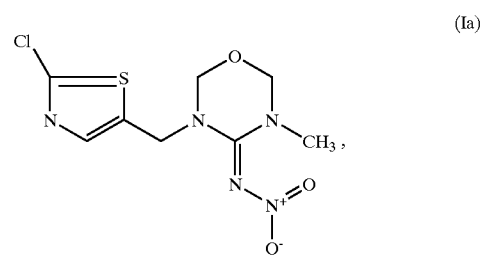

(Ia)

imidacloprid, (E)-1-(2-chlorothiazol-5-ylmethyl)-3-methyl-nitroguanidine (TI-435), nitenpyram, thiacloprid, and acetamiprid; particularly the compound of the formula (Ia) (thiamethoxam).

The alkyl, alkoxy or acyl groups of the formula (II) are preferably lower alkyl, alkoxy or acyl, that is to say radicals having one to four carbon atoms.

A preferred group of insecticidally effective 1-arylpyrazoles (II) of the present invention are those wherein:

$R_1$ and $R_2$ are a halogen atom, $R_3$ is 4-haloalkyl $R_4$ is lower haloalkyl and $R_5$ is amino.

A specific 1-arylpyrazole (H) usable in the compositions and methods falling within the scope of the present invention is fipronil.

The compounds of the formula (I) are known for instance from EP-A-580 553;

Imidacloprid is known from The Pesticide Manual, 11th Ed. (1997), The British Crop Protection Council, London, page 706;

Nitenpyram from The Pesticide Manual, 11th Ed. (1997), The British Crop Protection Council, London, page 880;

TI-435 from EP-A-376,279;

Thiacloprid from EP-A-235'725; and

Fipronil from The Pesticide Manual, 11th Ed. (1997), The British Crop Protection Council, London, page 545.

Fungicide Components (B)

Preferred are at least quaternary pesticidal compositions comprising as fungicidally active ingredient (B):

(B1) as first active ingredient at least one phenylamide (acylalanine type) of the formula (III):

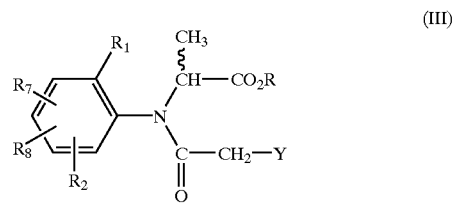

(III)

wherein $R_1$ is methyl; $R_2$ is in ortho position to the amino group and is methyl, ethyl or chlorine; $R_7$ and $R_8$ independently are hydrogen or methyl; R' is methyl; and Y is —OR$_4$ or —SR$_4$ in which R$_4$ is methyl, ethyl, propyl, isopropyl, butyl, sec. butyl or tert. butyl; and enantiomers thereof; in free from or in salt form.

Preferred phenylamide derivatives of formula (III) usable in the compositions and methods failing within the scope of the present invention include metalaxyl; metalaxyl consisting of more than 70% by weight of the R-enantiomer; metalaxyl consisting of more than 85% by weight of the R-enantiomer; metalaxyl consisting of more than 92% by weight of the R-enantiomer; metalaxyl consisting of more than 97% by weight of the R-enantiomer; and mefenoxam (i.e., R-metalaxyl or metalaxyl-M).

(B2) as second active ingredient at least one phenylpyrrole of the formula (IV):

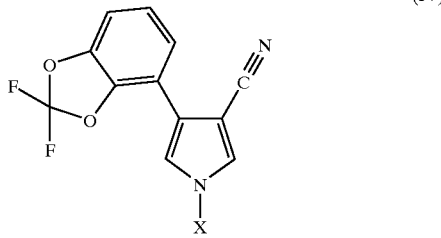

(IV)

wherein
is hydrogen or CO—$R_1$, wherein $R_1$ is $C_1$–$C_6$alkyl which is unsubstituted or substituted by halogen or $C_1$–$C_3$alkoxy; or is $C_3C_6$alkenyl, $C_3$–$C_6$alkynyl, or $C_1$–$C_6$alkoxy which is unsubstituted or substituted by halogen or $C_1$–$C_3$alkoxy; or is $C_3$–$C_6$alkenyloxy, or $C_3$–$C_6$cycloalkyl; in free from or in salt form.

A specific phenylpyrrole (IV) usable in the compositions and methods falling within the scope of the present invention is fludioxonil.

(B3) As third active ingredient at least one triazole of the formula (V):

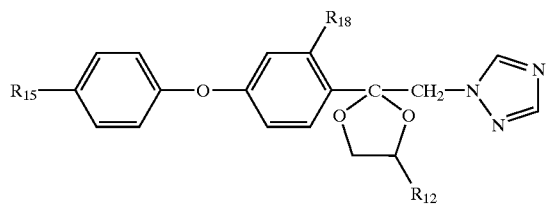

(V)

wherein
$R_{12}$, $R_5$ and $R_{18}$ are hydrogen, halogen, $C_1$–$C_3$alkyl, $C_1$–$C_3$alkoxy or nitro; in free from or in salt form.

A specific triazole (V) usable in the compositions and methods falling within the scope of the present invention is difenoconazole.

The compounds of the formula (III) are known for instance from U.S. Pat. No. 4,151,299;

The compounds of the formula (IV) from U.S. Pat. No. 4,705,800;

The compounds of the formula (V) from U.S. Pat. No. 5,266,58 5;

Difenoconazole is known from The Pesticide Manual, 10th Ed. (1994), The British Crop Protection Council, London, page 328;

Fludioxonil from The Pesticide Manual, 11th Ed. (1997), The British Crop Protection Council, London, page 566;

Metalaxyl from The Pesticide Manual, 11th Ed. (1997), The British Crop Protection Council, London, page 792; and R-metalaxyl (mefenoxam) from The Pesticide Manual, 11th Ed. (1997), The British Crop Protection Council, London, page 794.

A.I. Combination

Surprisingly, it has been found that the combination of the active ingredients (A), (B 1), (B2) and (B3) results in a quite unexpectedly enhanced action against insects or representatives of the order Acarina and microorganisms such as seed-borne and soil-borne fungi and/or provides other unexpected advantages when used in connection with plant propagation materials. The increase in action and/or other advantageous properties achieved with the combination according to the invention is significantly greater than the activity to be expected by the four individual components, i.e. the activity is enhanced synergistically which, inter alia, extends the boundaries of the pesticidal activity of the compounds.

In particular, it has now been found, surprisingly, that, for example, the pesticidal activity of the compositions according to the invention, compared with the pesticidal activity of the individual components, is not merely additive, as may essentially be expected, but that a synergistic effect exists. The term "synergistic" is not, however, in any way limited in this context to the pesticidal activity, but refers equally to other advantageous properties of the compositions according to the invention as compared with the individual components. Examples of such advantageous properties that may be mentioned are: a broadening of the spectrum of pesticidal activity to other pests, for example to resistant strains; a reduction in the rate of application of the active ingredients; adequate control of the pests with the aid of the compositions according to the invention, even at a rate of application at which the individual compounds are totally ineffective; advantageous behavior during formulating and/ or upon application, for example upon grinding, sieving, emulsifying, dissolving or dispersing; increased storage stability; improved stability to light; more advantageous degradability; improved toxicological and/or ecotoxicological behavior; improved crop characteristics including: emergence, crop yields, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, improved plant vigor, and early germination; or any other advantages familiar to a person skilled in the art.

In the area of pest control, the compositions according to the invention are valuable reductive (reducing the occurrence of a pest), preventive and/or curative active ingredients having a very advantageous biocidal spectrum even at low rates of concentration, while being well tolerated by warm-blooded animals, fish and plants. The compositions of the invention are effective against all or individual development stages of normally sensitive animal pests, but also of resistant animal pests, such as insects and representatives of the order Acarina, and phytopathogenic fungi. The insecticidal, acaricidal and/or fungicidal action of the compositions of the invention may manifest itself directly, i.e. in the mortality of the pests, which occurs immediately or only after some time, for example during molting, or indirectly, for example in reduced oviposition and/or a reduced hatching rate, the good activity corresponding to a mortality of at least 50 to 60%.

Advantageous mixing ratios of the at least four active ingredients are (A):(B1):(B2):(B3)=(250 to 50):(5 to 1):(2 to 1):(20 to 1), in particular (A):(B1):(B2):(B3)=(200 to 60):(3 to 1):(1.5):(10 to 1) and very particularly (A):(B1):(B2): (B3)=(160 to 120):(3 to 2):(1.2 to 1): (10 to 4). Other advantageous mixing ratios are (A):(B1):(B2):(B3)=(160): (3):(1):(9.6), or (120):(2):(1):(4.8).

The active ingredient combinations according to the invention preferably comprise a compound of formula (I) to (II), especially of the formula (I), more especially of the formula (Ia), and metalaxyl, fludioxonil and difenoconazole.

Preference is given especially to an active ingredient combination comprising the compound of formula (Ia), metalaxyl-M, fludioxonil and difenoconazole in a mixing ratio of (160):(3):(1):(9.6) or (400 g):(7.5 g):(2.5 g):(24 g).

Other preferred ratios include: (200 g):(3.75 g):(1.25 g):(12 g) and (500 g):(7.5 g):(2.5 g):(24 g).

The above-mentioned mixing ratios relate on the one hand to parts by weight of the individual components, but on the other hand also to the mixing ratios in moles. Thus, for example, with respect to the previous paragraph the ratio of (250 to 50):(1):(1):(1) denotes from about 250 to about fifty parts by weight of a compound of formula (Ia) to one part by weight of a each of metalaxyl-M, fludioxonil and difenoconazole; but also from about 250 to about fifty moles of a compound of formula (Ia) to one mole of a each of the compounds metalaxyl-M, fludioxonil and difenoconazole. In addition, it will be understood that 1 part by weight may equal the actual weight of the active component with the lowest loading. For example, a mixing ratio of (160):(3):(1) :(9.6) parts would equal the ratio (400 g):(7.5 g):(2.5 g):(24 g) in grams (wherein 2.5 grams is considered "1 part"). Finally, the figures relate also to mixtures in the ratio of the $LD_{50}$ values of the individual pests to be controlled.

In one embodiment, the application rate utlizing the above-noted mixing ratios is calculated per 100 kilograms of seed or other plant propigation material to be treated.

Fungal Pests

The compositions according to the invention are especially active against fungi, in particular of the oomycetes which belong to the class of phycomycetes (e.g., phytophthora, peronospora, pseudoperonospora, pythium sp. or plasmopara), basidiomycete, ascomycete, adelomycete or Fungi Imperfecti type, such as *Botrytis cinerea, Erysiphe graminis, Puccinia graminis, Puccinia recondita, Piricularia oryzae, Cercosoora beticola, Puccinia striiformis, Erysiphe cichoracearum, Rhinchosporium secalis, Fusarium, Solani, Fusarium oxysporum* (e.g. melonis), *Pyrenophora avenae, Septoria tritici, Septoria avenae, Whetzelinia sclerotiorum, Mycosohaerella fijiensis, Alternaria solani, Aspergillus niger, Cercospora arachidicola, Cladosporium herbarum,Tilletia caries, Tilletia contreversa, Fusarium roseum, Fusarium nivale, Helminthosporium oryzae, Helminthosporium teres, Helminthosporium gramineum, Helminthosporium sativum, Penicillium expansum,* Pestalozzia sp, *Phoma betae, Phoma foveata, Phoma lingam, Ustilago maydis, Ustilago nuda, Ustilago hordei, Ustilago avenae, Verticillium dahliae, Ascochyta pisi, Guignardia bidwellii, Corticium rolfsii, Phomposis viticola, Sclerotinia sclerotiorum, Sclerotinia minor, Coryneum cardinale, Rhizoctonia solani, Acrostalagmus koningi,* Alternaria, Colletotrichum, *Corticium rolfsii, Diplodia natalensis, Gaeumannomyces graminis, Gibberella fujikuroi, Hormodendron cladosporioides, Myrothecium verrucaria, Paecylomyces varioti, Pellicularia sasakii, Phellinus megaloporus, Scierotium rolfsii, Stachybotris atra, Trichoderma pseudokoningi, Trichothecium roseum.*

The compositions according to the invention are particularly suited for the reductive, preventive and the curative protection of the plant propagation material against fungi and fungal diseases including: damping off (e.g., Fusarium sp., Pythium sp., Rhizoctonia sp.), root rot (e.g., Pythium sp., Fusarium sp., Gibberella sp.), and seed or soil borne blackleg (Leptosphaeria maculans) diseases of vegetable organisms and plants in general, and especially of oil seed crops such as canola (rape), mustard seed, and hybrids thereof, and also rice and maize.

Insect Pests

The compositions according to the invention may be used for the protection of the plant propagation material and developing plants against animal pests such as insects and representatives of the order Acarnia including:

from the order Lepidoptera, for example,
Acleris spp., Adoxophyes spp., Aegeria spp., Agrotis spp., *Alabama argillaceae,* Amylois spp., *Anticarsia gemmatalis,* Archips spp., Argyrotaenia spp., Autographa spp., *Busseola fusca, Cadra cautella, Carposina nipponensis,* Chilo spp., Choristoneura spp., *Clysia ambiguella,* Cnaphalocrocis spp., Cnephasia spp., Cochylis spp., Coleophora spp., *Crocidolomia binotalis, Cryptophlebia leucotreta,* Cydia spp., Diatraea spp., *Diparopsis castanea,* Earias spp., Ephestia spp., Eucosma spp., *Eupoecilia ambiguella,* Euproctis spp., Euxoa spp., Grapholita spp., *Hedya nubiferana,* Heliothis spp., *Hellula undalis, Hyphantria cunea, Keiferia lycopersicella, Leucoptera scitella,* Lithocollethis spp., *Lobesia botrana,* Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,* Pieris spp., *Plutella xylostella,* Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

from the order Coleoptera, for example,
Agriotes spp., Anthonomus spp., *Atomaria linearis, Chaetocnema tibialis,* Cosmopolites spp., Curculio spp., Dermestes spp., Diabrotica spp., Epilachna spp., Eremnus spp., *Leptinotarsa decemlineata,* Lissorhoptrus spp., Melolontha spp., Orycaephilus spp., Otiorhynchus spp., Phlyctinus spp., Popillia spp., Psylliodes spp., Rhizopertha spp., *Scarabeidae, Sitophilus* spp., Sitotroga spp., Tenebrio spp., Tribolium spp. and Trogoderma spp.;

from the order Orthoptera, for example,
Blatta spp., Blattella spp., Gryllotalpa spp., Leucophaea maderae, Locusta spp., Periplaneta spp. and Schistocerca spp.;

from the order Isoptera, for example,
Reticulitermes spp.;

from the order Psocoptera, for example,
Liposcelis spp.;

from the order Anoplura, for example,
Haematopinus spp., Linognathus spp., Pediculus spp., Pemphigus spp. and Phylloxera spp.;

from the order Mallophaga, for example,
Damalinea spp. and Trichodectes spp.;

from the order Thysanoptera, for example,

Frankliniella spp., Hercinothrips spp., Taeniothrips spp., *Thrips palmi, Thrips tabaci* and *Scirtothrips aurantii;* from the order Heteroptera, for example,

Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

from the order Homoptera, for example,

Aleurothrixus floccosus, Aleyrodes brassicae, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* from the order Hymenoptera, for example,

Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

from the order Diptera, for example,

Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;

from the order Siphonaptera, for example,

Ceratophyllus spp. und *Xenopsylla cheopis* and from the order Thysanura, for example,

*Lepisma saccharina.*

The active ingredients according to the invention are particularly suitable for controlling crucifer flea beetles (Phyllotreta spp.), root maggots (Delia spp.), cabbage seedpod weevil (Ceutorhynchus spp.) and aphids in oil seed crops such as canola (rape), mustard seed, and hybrids thereof, and also rice and maize.

Target Crops

Target crops within the scope of this invention are, for example, the following plant species: beet (sugar beet and fodder beet), oil plants (canola, rape, mustard seed, poppy, olives, sunflowers, coconut, castor oil plants, cocoa beans, groundnuts and soya). There also may be mentioned peanuts, wheat sorghum and corn.

In addition, the crops listed in the crop group tables in 40 CFR Sec. 180.41 (1995) are noted. 40 CFR Sec. 180.41 (1995) and the Federal Register: May 17, 1995 (vol. 60, no. 95) pp. 26625–26643 are fully incorporated by reference herein for their disclosure relating to useful crop plants:

(1) Crop Group 5: Brassica (Cole) Leafy Vegetables Group, for example, broccoli, cauliflower; cabbage; and mustard greens;

(2) Crop Group 9: Cucurbit Vegetables Group, for example, cucumber, muskmelon and summer squash;

(3) Crop Group 11: Pome Fruits Group, for example, apple and pear;

(4) Crop Group 15: Cereal Grains Group, for example, corn and rice.

The following plants are to regarded as being particularly suitable target crops for the at least quaternary pesticide compositions of the invention: plant propagation materials (such as seeds) of oil plants (canola, rape, mustard seed, poppy, olives, sunflowers, coconut, castor oil plants, cocoa beans, groundnuts).

The seeds treated in accordance with the invention include conventional as well as genetically enhanced or engineered varieties such as, for example, insect resistant (e.g., Bt.) as well as disease resistant varieties.

Seed Treatment

The at least quaternary pesticidal composition according to the invention has proved especially advantageous for protecting seeds, in particular, oil seeds such as canola. However, the inventive composition is also suitable for direct treatment of the soil or of other parts of the plant. The inventive composition is well tolerated by plants, and is ecologically acceptable.

The subject of the invention is also a method for protecting the multiplication products of plants (plant propagation materials) and the plants resulting therefrom against insects and fungal diseases, wherein the said multiplication products are coated with an insecticidal and fungicidal and non-phytotoxic composition according to the invention.

The at least quaternary pesticidal composition according to the invention is usually employed together with the adjuvants customary in formulation technology. The combination of the active ingredients (A), (B 1), (B2) and (B3) are normally applied to plant propagation material in the form of compositions, but also can be applied to the seed or to the locus of propagation thereof (such as a furrow), simultaneously or in succession, with further compounds. These further compounds can be fertilizers or micronutrient donors or other preparations that influence plant growth. They can also be selective herbicides, insecticides, fungicides, bactericides, insect growth regulators, plant growth regulators, nematicides, molluscicides or mixtures of several of these preparations, if desired, together with further carriers, surfactants or application-promoting adjuvants customarily employed in the art of formulation. In addition, there may be mentioned inoculants, brighteners and polymers.

This invention also includes suitable agricultural compositions for controlling insects and fungi on or in seed consisting essentially of at least quaternary pesticidal composition of this invention plus a suitable inert surfactant or an suitable inert liquid or a solid carrier. As used herein, the phrase "consisting essentially of" does not exclude the presence of other active pesticidal materials or conventional formulating ingredients.

The active components (A), (B 1), (B2) and (B3) are processed in known manner to give, for example, emulsifiable concentrates, suspoemulsions, spreadable pastes, directly sprayable or dilutable solutions, dilute emulsions, wettable powders, soluble powders, dusts, granules, and also for encapsulation in, for example, polymeric substances. The application methods, such as spraying, misting, atomising, broadcasting, brushing or pouring, and the nature of the composition are adapted to suit the intended aims and the prevailing circumstances. In general, favorable rates of application are 0.0005 to not more than 0.5 kg, in particular 0.001–0.03 kg of each active ingredient (B1), (B2) and (B3) per 100 kg of material to be protected. With respect to the active ingredient (A), the favorable rates of application can range from 0.005 to not more than 1 kg, in particular 0.01–0.8 kg, more particularly 0.1–0.5 kg per 100 kg of material to be protected. However, the application conditions depend essentially on the nature (surface area, consistency, moisture content) of the material and on its environmental factors. Accordingly, within these ranges, those skilled in the art will choose, on the basis of their general body of knowledge and, where appropriate, a few experiments, doses which are non-phytotoxic but effective from a fungicidal and/or insecticidal standpoint.

The term "plant propagation material" is understood to denote al the generative parts of the plant such as seeds which can be used for the multiplication of the latter and vegetative plant material such as cuttings and tubers (for example potatoes). There may be mentioned, e.g., the seeds (in the strict sense), roots, fruits, tubers, bulbs, rhizomes, parts of plants. Germinated plants and young plants which are to be transplanted after germination or after emergence from the soil, may also be mentioned. These young plants may be protected before transplantation by a total or partial treatment by immersion.

Also within the scope of the present invention, storage goods which can be protected with the mixture according to the invention, in particular plant propagation material, especially seeds, will be understood as meaning natural substances of vegetable and/or animal origin and their processing products for which long-term protection is desired, for example the plants and parts thereof, which are mentioned below (stalks, leaves, tubers, seeds, fruits, grains) which have been taken from the natural life cycle and which exist in the freshly harvested state or in processed form (pre-dried, moistened, comminuted, ground, pressed, roasted, etc.). Also falling within the scope of the invention is the protection of timber, whether in the form of crude timber (construction timber, electricity pylons, barriers) or in the form of finished articles (furniture, objects made from wood). Natural products of animal origin which are to be preserved, for example hides, furs, hairs and the like, likewise fall within the scope of the invention.

The techniques of seed treatment application are well known to those skilled in the art, and they may be used readily in the context of the present invention. The active ingredients can be formulated and applied as a slurry, a solid seed coating, a soak, or as a dust on the surface of the seed. There also may be mentioned, e.g., film-coating or encapsulation. The coating processes are well known in the art, and employ, for seeds, the techniques of film-coating or encapsulation, or for the other multiplication products, the techniques of immersion. Needless to say, the method of application of the compounds to the seed may be varied and the invention is intended to include any technique which is to be used.

A preferred method of applying the mixture according to the invention consists in spraying or wetting the plant propagation material with a liquid preparation, or mixing the plant material with a solid preparation of the active ingredients.

The compounds of this invention may be formulated or mixed in the seed treater tank or combined on the seed by overcoating with other seed treating agents. The agents to be mixed with the compounds of this invention may be for the control of pests, modification of growth, nutrition, or for the control of plant diseases.

Formulations

The formulations, i.e. the compositions, preparations or combinations containing the active ingredients (A), (B1), (B2) and (B3), as well as, if appropriate, suitable inert solid or liquid carriers, are prepared in a known manner, for example by intimately mixing and/or grinding the active ingredients with inert, agriculturally-acceptable extenders, for example with solid or liquid carriers and, if appropriate, surface-active compounds (surfactants). Such compositions may be advantageously formulated as flowable compositions, suspensions, microsuspensions, suspoemulsions, wettable powders, granulated concentrates, microemulsions and the like, all of which lend themselves to seed treatment application and provide the requisite plant protection.

The term "carrier" in the present description denotes a natural or synthetic, organic or inorganic material with which the active substance is combined in order to facilitate its application to the plant, to the seeds or to the soil. This carrier is hence generally inert, and it must be agriculturally acceptable, in particular to the plant being treated. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

Suitable liquid carriers are: aromatic hydrocarbons, in particular the fractions $C_8$ to $C_{12}$, such as xylene mixtures or substituted naphthalenes, phthalic esters such as dibutly or dioctyl phthalate, aliphatic hydrocarbons such as cyclohexane or paraffins, alcohols and glycols as well as their ethers and esters, such as ethylene glycol monomethyl ether, ketones such as cyclohexanone, strongly polar solvents such as N-methyl-2-pyrrolidone, dimethyl sulfoxide or dimethylformamide, and, if appropriate, epoxidized vegetable oils or soybean oil; or water.

Solid carriers which may be used, for example for dusts and dispersible powders, are calcite, talc, kaolin, montmorillonite or attapulgite, highly-disperse silica or absorptive polymers. Possible particulate, adsorptive carriers for granules are pumice, crushed brick, sepiolite or bentonite, montmorillonite-type clay, and possible nonsorbent carrier materials are calcite or dolomite.

Suitable surface-active compounds are non-ionic, cationic and/or anionic surfactants having good emulsifying, dispersing and wetting properties, depending on the nature of the active ingredients (A), (B1), (B2) and (B3) to be formulated. Surfactants will also be understood as meaning dmixtures of surfactants.

The surfactants customarily employed in formulation technology are described, inter alia, in the following publications:

"McCutcheon's Detergents and Emulsifiers Annual", MC Publishing Corp., Glen Rock, N.J., 1988.

M. and J. Ash, "Encyclopedia of Surfactants", Vol. I-III, Chemical Publishing Co., New York, 1980–1981.

Among the suitable surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols. The presence of at least one surfactant is often required because the active substance and/or the inert vehicle are not soluble in water and the carrier agent for the application is water.

Furthermore, particularly useful adjuvants which enhance application are natural or synthetic phospholipids from the series of the cephalins and lecithins, for example phosphatidylethanolamine, phosphatidyiserine, phosphatidylglycerine or lysolecithin.

The agrochemical compositions generally contain: 0.1 to 99%, in particular 9 to 50%, more particularly 20 to 25% of the active substances (A), (B1), (B2) and (B3); the balance of the formulation comprising a solid and/or liquid carrier along with optional surfactant(s) and other optional inert ingredients known in the art such as, e.g., protective colloids, adhesives, thickeners, thixotropic agents, penetrating agents, preservatives, stabilizers, antifoaming agents, antifreeze agents, sequestering agents, dyes, pigments, colorings and polymers.

In one embodiment, commercial products will preferably be formulated as concentrates whereas the end user will normally use dilute formulations.

FORMULATION EXAMPLES

%=Per Cent by Weight

The examples which follow are intended to illustrate and not limit the invention, "active ingredient" being understood as meaning a mixture of the active substances (A), (B1), (B2) and (B3) in a particular mixing ratio of (A):(B1):(B2):(B3)=(160 to 120):(3 to 2):(1.2 to 1):(10 to 4).

| Example F1: Emulsifiable concentrates | a) | b) | c) |
|---|---|---|---|
| active ingredients | 25% | 40% | 50% |
| calcium dodecylbenzenesulfonate | 5% | 8% | 6% |
| castor oil polyethylene glycol ether | 5% | — | — |
| tributylphenol polyethylene glycol ether | — | 12% | 4% |
| cyclohexanone | — | 15% | 20% |
| xylene mixture | 65% | 25% | 20% |

Emulsions of any desired concentration can be prepared from this concentrate by dilution with water, and can be employed in crop protection and in seed treatment applications.

| Example F2: Dusts | a) | b) |
|---|---|---|
| active ingredients | 5% | 8% |
| talc | 95% | — |
| kaolin | — | 92% |

Ready-to-use dusts are obtained by mixing the active ingredients with the carrier and grinding the mixture in a suitable mill. Such powders can be used for dry-dressing seeds.

| Example F3: Wettable powders | a) | b) | c) |
|---|---|---|---|
| active ingredients | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether | — | 2% | — |
| highly dispersed silicic acid | 5% | 10% | 10% |
| kaolin | 62% | 27% | — |

The active ingredient is mixed thoroughly with the additives and the mixture is ground thoroughly in a suitable mill affording wettable powders which can be diluted with water to give suspensions of any desired concentration. Such slurries can be used for carrying out furrow treatments on prior to planting crops of plants and also for wet- or moist-dressing material which can be propagated, for example oil seeds or tubers of plants.

| Example F4: Suspoemulsions | a) |
|---|---|
| active ingredients | 22.5% |
| sulfated nonylphenol (polyoxyethylene condensate) | 0.1% |
| phosphated tristyrylphenol (polyoxyethylene condensate) | 4% |
| sodium lignosulfonate (polyoxyethylene condensate) | 2% |
| NaOH (50%) | 0.1% |
| silicone defoaming agent | 0.1% |
| pigment(s) | 9.5% |
| glycerin | 20% |
| xanthan gum | 0.2% |
| water | 41.5% |

This formulation is suitable for mixtures of solid and liquid active ingredients. The solid active ingredient(s) are mixed thoroughly with a portion of the emulsifiers and water and the mixture is ground thoroughly in a suitable mill. Another portion of the emulsifiers and water are mixed with the liquid active ingredient(s). The two mixtures are combined along with any other inert ingredients (such as pigments, thickeners, etc.) that are to be used in the formulation. Such suspoemulsions can be used for carrying out in furrow treatments prior to planting crops of plants and also for wet- or moist-dressing material which can be propagated, for example oil seeds or tubers of plants.

BIOLOGICAL EXAMPLES

Biological Examples %=Per Cent by Weight Unless Otherwise Indicated

The examples which follow are intended to illustrate and not limit the invention. The pesticidal composition of the invention used in the examples comprises the following active ingredient (a.i.) mixture used at the noted application rate:

| Active Ingredient Mixture | | Application Rate (grams a.i./100 kg seed) |
|---|---|---|
| (A) | Thiamethoxam | 400 |
| (B1) | Mefenoxam | 7.5 |
| (B2) | fludioxonil | 2.5 |
| (B3) | difenconazole | 24 |

Example B1: Emergence

Canola seed is treated with the pesticidal composition of the invention the rates given above and is seeded following procedures which correspond to conditions found in practice. Untreated seeds from the same origin are used for comparison purposes. Emergence (plants per meter) is evaluated.

TABLE B1

| Treated Seed | Untreated Seed |
|---|---|
| 23 plants/m | 18 plants/m |

Example B2

Vigor

Canola seed is treated with the pesticidal composition of the invention at the rates given above and is seeded following procedures which correspond to conditions found in practice under high crucifer flea beetle pressure. Untreated seeds from the same origin are used for comparison purposes. Plant vigor (1–2 leaf stage) is evaluated.

TABLE B2

| Treated Seed | Untreated Seed |
|---|---|
| 94% | 18% |

Example B3

Yields

Canola seed is treated with the pesticidal composition of the invention at the rates given above and is seeded following procedures which correspond to conditions found in practice. The crop is harvested from the field at maturity. Untreated seeds from the same origin are used for comparison purposes. Crop yield (bushels per acre) is evaluated.

TABLE B3

| Treated Seed | Untreated Seed |
|---|---|
| 43 (bu/ac) | 28 (bu/ac) |

In summary, it is seen that this invention provides a new at least quaternary pesticidal composition for the protection of plant propagation materials. Variations may be made in proportions, procedures and materials without departing from the scope of the invention as defined by the following claims.

We claim:

1. A quaternary pesticide composition comprising as active ingredients: synergistic pesticidally effective amounts ofbthe mixture of
   (A) an insecticidally or acaricidally effective amount of a compound of the fomula (I),

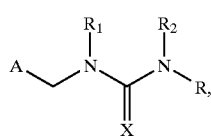

(I)

wherein
A is 2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyl-tetrahydrofuran-3-yl or 2-chlorothiazol-5-yl group, R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl;

$R_1$ and $R_2$ are independently of each other $C_1$–$C_4$-alkyl, $C_1$–$C_4$-alkenyl, $C_1$–$C_4$-alkinyl, $C_1$–$C_4$-alkinyl, —C(=O)—$CH_3$ or benzyl; or together form a group —$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$— or —$CH_2$—N($CH_3$)—$CH_2$—; and X is N—$NO_2$ or N—CN or CH—$NO_2$;, or, where appropriate, a tautomer thereof, in each case in free from or in salt form;

(B) a fungicidally effective amount of the three fungicides mefenoxam (B1), fludioxonil (B2) and difenoconazole (B3); or in salt form; together with a suitable carrier therefor wherein the ratio of (A) to each of the three fungicides, B1, B2 and B3 is in the ratio of (A):(B1):(B2):(B3) of (250 to 50):(5 to 1):(2).

2. A composition according to claim 1 which contains (A) an insecticidally or acaricidally effective amount of a compound selected from the group consisting of: a compound of the

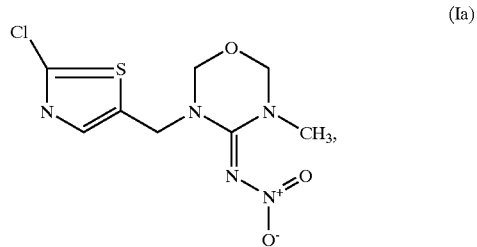

(Ia)

imidacloprid, (E)-1-(2-chlorothiazol-5-ylmethyl)-3-methyl-nitroguanidine (TI-435), nitenpyram, thiacloprid, and acetamiprid.

3. A composition according to claim 2 which contains (A) an insecticidally or acaricidally effective amount of a compound of the formula

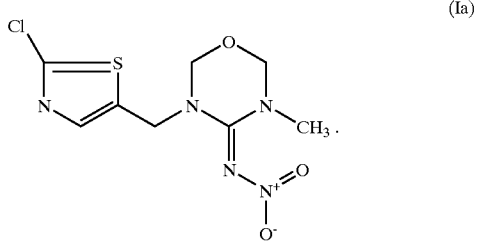

(Ia)

4. A composition according to claim 1 wherein the ratio of active ingredients (A):(B1):(B2):(B3) is (400 g):(7.5 g):(2.5 g):(24 g).

5. Pest-resistant plant propagation material comprising plantkpropagation material treated with a synchgisble pesticidally effective amount of a pesticidal composition claim 1.

6. A pest-resistant plant propagation material according to claim 5 wherein said pesticidal composition contains (A) an insecticidally or acaricidally effective amount of a compound selected from the group consisting of: a compound of the formula

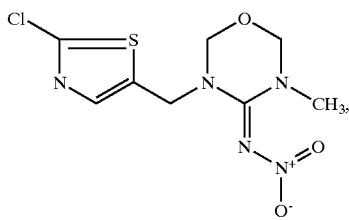 (Ia)

imidacloprid, (E)-1-(2-chlorothiazol-5-ylmethyl)-3-methyl-nitroguanidine (TI-435), nitenpyram, thiacloprid, and acetamiprid.

7. A pest-resistant plant propagation material according to claim 6 wherein said pesticidal composition contains (A) an insecticidally or acaricidally effective amount of a compound of the

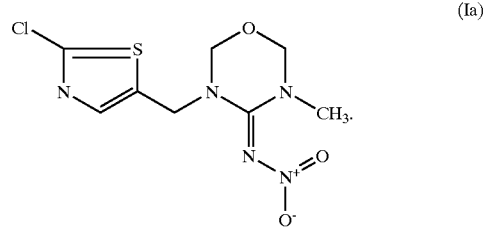 (Ia)

8. A pest-resistant plant propagation material according to claim 5 wherein the ratio of active ingredients (A):(B1):(B2):(B3) in said pesticidal composition is (400 g):(7.5 g):(2.5 g):(24 g).

9. A method of protecting plant propagation material against against attack by insects or representatives of the order order Acarina and phytopathogenic fungi which comprises treating said plant propagation material with a synergistie insecticidally (or acaricidally) and fungicidally effective amount of a composition according to claim 1.

10. A method according to claim 9 wherein said plant propagation material is a plant seed selected from the group consisting of canola, rape, mustard seed, poppy, olives, sunflowers, coconut, castor oil plants, cocoa beans, groundnuts.

* * * * *